(12) United States Patent
Hemati et al.

(10) Patent No.: US 10,258,436 B2
(45) Date of Patent: Apr. 16, 2019

(54) METHOD AND SYSTEM FOR TRANSFERRING SIGNALS AND MATERIALS BETWEEN INSIDE AND OUTSIDE BODY THROUGH ORAL CAVITY

(71) Applicants: Saied Hemati, Moscow, ID (US); Sepideh Rahmani, Moscow, ID (US)

(72) Inventors: Saied Hemati, Moscow, ID (US); Sepideh Rahmani, Moscow, ID (US)

( * ) Notice: Subject to any disclaimer, the term of this patent is extended or adjusted under 35 U.S.C. 154(b) by 0 days.

(21) Appl. No.: 14/739,556

(22) Filed: Jun. 15, 2015

(65) Prior Publication Data

US 2015/0374462 A1 Dec. 31, 2015

Related U.S. Application Data

(60) Provisional application No. 62/012,421, filed on Jun. 16, 2014.

(51) Int. Cl.
*A61C 8/00* (2006.01)
*A61N 1/00* (2006.01)
*A61C 19/04* (2006.01)

(52) U.S. Cl.
CPC ............ *A61C 8/0093* (2013.01); *A61C 19/04* (2013.01); *A61B 2560/0204* (2013.01); *A61C 8/0022* (2013.01); *A61C 8/0031* (2013.01)

(58) Field of Classification Search
CPC ...... A61C 8/0007; A61C 13/0015; A61C 5/08
See application file for complete search history.

(56) References Cited

U.S. PATENT DOCUMENTS

| | | | |
|---|---|---|---|
| 2010/0143871 A1* | 6/2010 | Berger | A61B 17/8605 433/174 |
| 2012/0064486 A1* | 3/2012 | Sobrado Marinho | A61B 5/228 433/173 |
| 2014/0058330 A1* | 2/2014 | Boe | A61C 8/0039 604/174 |

* cited by examiner

*Primary Examiner* — Amanda K Hulbert
*Assistant Examiner* — Natasha Patel
(74) *Attorney, Agent, or Firm* — Duncan Palmatier

(57) ABSTRACT

This invention discloses a physical gateway that goes directly through gum or other soft tissues inside the oral cavity, to access inside body. The physical gateway has parts acting as external access points that have terminals for cables, wires, fiber optics, or tubes that go through said gateways to implanted medical systems and devices to facilitate transmission of signals or materials to or from said implanted systems or devices. This feature can be used for powering implanted systems and devices with high functionality and computation power, securely communicating with implanted systems and devices with vital duties, and transferring materials for refilling the tanks in implanted systems and devices or for transferring some material from inside body to outside without requiring invasive operations.

8 Claims, 5 Drawing Sheets

METHOD AND SYSTEM FOR TRANSFERRING SIGNALS AND MATERIALS BETWEEN INSIDE AND OUTSIDE BODY THROUGH ORAL CAVITY

CROSS-REFERENCE TO RELATED APPLICATION

This patent application claims the benefit of U.S. Provisional Patent Application U.S. 62/012,421 filed on Jun. 16, 2014 entitled "Method and System for Transferring Signals and Materials between Inside and Outside Body through Oral Cavity".

STATEMENT REGARDING FEDERALLY SPONSORED RESEARCH AND DEVELOPMENT

Not Applicable

BACKGROUND OF THE INVENTION

1. Field of the Invention

This invention relates to implantable medical devices and dental implants and discloses a system and method for transferring signals (electrical, optical, chemical, mechanical, magnetic, and similar signals used for delivering energy, data messages and to control, monitor, sense, treat, heat or cool, and for any other applications) and materials (in any shape in solid, liquid, gas, plasma forms used for delivering energy, data messages, blood and its components, medications, clinical samples and to heat or cool, drain, control, monitor, sense, treat and for any other applications) between outside and inside body through oral cavity.

2. Background Art

Implantable medical devices and systems are projected to revolutionize the healthcare system by providing new opportunities for solving previously intractable health problems via immediate symptom detection and instantly responsive intervention. Implantable medical devices and systems are expected to increase the life expectancy by constantly assessing vital biochemical parameters and electric signals within the human body and detecting and reporting any symptom at its appearance. Upon diagnosis, treatment will be delivered by an implantable device which will eliminate under and overdosing medication or by implanting an artificial body system interface to restore normal function.

One of the most promising applications will benefit hundreds of millions of diabetic patients by constantly monitoring their blood sugar and providing insulin at the right time and dosage without need for painful injections. These devices also have the potential to play a significant role in improving the quality of life for patients with spinal cord injuries by serving as an interface between the nervous system and muscles (or possibly artificial actuators).

BRIEF SUMMARY OF THE INVENTION

1—Technical Problem

Battery operated implantable medical devices have long been used in cardiac pacemakers to help control abnormal heart rhythms. However, battery operated devices suffer from short lifespan. In fact, small energy capacity of available batteries makes them suitable only for low-power applications and require battery replacement every few years, which often involves invasive surgeries. Failure of the battery can also be fatal. Similar problems exist for any battery-operated implantable device and system.

An alternative approach relies on electromagnetic induction similar to basic transformers with the secondary coil placed inside the chest or abdomen. This techniques have long been considered for powering artificial heart assists and pacemakers and is able to deliver tens of watts of power to implanted devices. This technique relies on bulky coils and requires major invasive surgeries to install the secondary coil and the related electronic circuits and the backup battery inside the body.

Implanted heart assists can also be powered using cables that go directly through the skin in chest or abdomen, however, it is only a short term solution which easily causes infection and is rather inconvenient and a painful experience for the patient.

More recently, there have been some attempts for developing energy harvesting techniques to generate power inside body by converting thermal, mechanical, chemical, electromagnetic, and optical energy. However, these techniques often generate a small amount of power that are only suitable for very low-power applications, which inevitably limits the functionality of the implantable devices.

An example of conventional battery operated low-power implanted devices with the option of inductively charging the battery was given in U.S. Patent Pub. No. US 2010/0143871 A1, filed on Feb. 4, 2010, which discloses a self-powered osteogenesis-inducing dental screw-type implant that can generate electrical stimulation signals. Electrical stimulation facilitates speed healing of the screwed implant surgical site and promotes bone healing and bone formation near the dental implant. During the healing process, a bone-growth-stimulator healing abutment (230 in its FIG. 4 and FIG. 8) is used that includes a hermetically sealed casing (40 in its FIG. 1 and FIG. 4) that accommodates a rechargeable battery and electric circuits to create a cathode (52 in its FIG. 1 and FIG. 4) near the tip of a cannulated threaded (preferably non-conductive) dental screw implant (20 in its FIG. 2, FIG. 3, FIG. 6, FIG. 8, and FIG. 9) and an anode at the proximal end (casing 40 in its FIG. 1 and FIG. 4) to generate a small constant current between the anode and the cathode with a magnitude of 5 µA to 50 µA to stimulate bone formation to reduce the healing time required before attachment of prosthetic dentition. After bone healing has been completed, the bone-growth-stimulator healing abutment (230 in its FIG. 4 and FIG. 8) is replaced with a permanent prosthetic tooth (240 in its FIG. 5), or bosses (250 in its FIG. 9) by which a bridgework can be affixed. It has also been contemplated that RFID technology and/or biological sensors may be incorporated into the device, i.e., the casing (40 in its FIG. 1 and FIG. 4) can be additionally be provided with a temperature sensor (70 not shown in any of its figures), a pressure sensor (72 in its FIG. 4), a pH sensor (74 in its FIG. 4), a global positioning sensor (76 in its FIG. 4) or a microorganism sensor (78 in its FIG. 4) which are housed in the casing chamber. Rechargeable lithium batteries are an alternative way to power the bio implantable microsystem wherein the battery (44 in its FIG. 4 and FIG. 7) is inductively charged thereby eliminating the necessity for battery replacement.

Any implantable device with high computational and analyzing power will inevitably consume significant energy, which is orders of magnitude higher than what energy harvesting techniques within the human body can provide.

Beyond energy delivery, security in transmission of commands, control signals, and sensitive information to and from smart implanted devices is always a concern. Hacking and cyber-attacks can be lethal in case of implantable devices capable of monitoring and controlling vital organs. In particular, wireless communication systems, which rely on propagation of unguided electromagnetic waves, are not immune to unauthorized access of third parties and thus are vulnerable to cyber-attacks. Guided communications, when signal are confined to cable, wires, optical fibers, other wave-guides, or similar media are immune to cyber-attacks by limiting the physical access to the sensitive information. However, no viable approach existed before this invention for permanently and securely accessing the implantable devices via cables, wires, optical fibers, and other wave-guides.

Beyond power and signal delivery, it is desirable to establish a permanent gateway for delivering some material to inside body or transferring some material from inside body to outside. For instance, delivering medication to patients (for example insulin for diabetic patients) at the right time and dosage without painful injections using implanted systems and devices (ISAD) is highly desirable. However, currently there is no easy way for refilling the storage of an implanted device by proper medication. It is also very desirable to acquire samples from inside body for detailed investigations without performing invasive surgeries.

2—Solution to Problem

This invention solves said problems by creating physical gateways that go directly through gum or other soft tissues inside the oral cavity, to access inside body. Some parts of said physical gateways are permanently placed in a) jaw-bones b) any other bones in close vicinity of oral cavity c) beneath the gum and other soft tissues inside oral cavity but not necessarily inside any bone. Said physical gateways have parts acting as external access points that directly go through the gum and other soft tissues inside the oral cavity to become externally accessible. The external access points have terminals for cables, wires, fiber optics, or tubes that go along the way through said gateways to implanted health monitoring/controlling systems and devices to facilitate transmission of signals or materials to or from said implanted systems or devices. Said implanted health monitoring/controlling systems and devices (ISAD) can perform different tasks and can be placed anywhere within the body including, soft tissues, organs, skull, brain, neck, chest, abdomen, legs, and arms. Said implanted health monitoring/controlling systems and devices can have large power consumption much higher than what energy harvesting techniques can provide.

Said terminals in said external access point are easily accessible by the patient and medical staffs to charge batteries in implanted health monitoring/controlling devices and systems (ISAD), securely communicate with said implanted health monitoring/controlling devices and systems (ISAD) and send and receive the vital control and information messages. Transfer materials between outside the body and said implanted health monitoring/controlling devices and systems (ISAD) if it is required. Said material can be any material of interest such as medication that is transferred to the implanted health monitoring/controlling devices and systems (ISAD), for instance to fill a medication storage or tank. Said material can be any form of samples taken from inside body sent outside for further examination and for other reasons.

Said physical gateway and said external access points are made, coated, covered, or enveloped partly or totally with materials such as titanium or other biocompatible materials that integrate with bones and cause no infection in gum and other soft tissues in oral cavity. Said cables, wires, tubes are made, coated, covered, or enveloped partly or totally with materials such as titanium or other biocompatible materials that cause no infection in bones, gum, and other tissues and organs in their path to said implanted health monitoring/controlling systems and devices (ISAD).

Another aspect of this invention is in merging said external access point and said gateway with a dental implant to have a better appearance and help in chewing. This is an interesting solution for patients who need a dental implant too. In a specially designed dental implant, the abutment and the crown can be removed whenever required to access the terminals located beneath the abutment. The abutment and crown can be screwed to the physical gateway that also acts as the fixture of the dental implant in this case. The abutment and crown can be removed and placed back as many times as required.

The currently available screw-type abutments can be used for this purpose but with some modifications to strengthen the screws as they are currently designed to be opened and closed only a few times. The fixture should, however, be altered to become hollow in order to accommodate cables, wires, and tubes.

The crown can also be securely screwed to a modified abutment from lingual side or palatal side not to impact the crown's look. The modified abutment let the screw keep the crown tightly attached to abutment.

3—Advantageous Effects of Invention

This invention paves the way for development of highly capable implantable health monitoring/controlling systems and devices (ISAD) acting as a small clinic located inside body with capabilities in clinical testing, monitoring vital organs, medication delivery, taking samples from suspicious materials and delivering it to outside of the body, controlling artificial organs and actuators, draining harmful liquids, warming or cooling some organs and other applications. This invention teaches how to build a permanent gateway for transferring signals and materials and accessing inside body, which is vital part of any advanced implantable system and device (ISAD).

The invention presents a safe, convenient, inexpensive gateway for accessing inside body in order to transfer signals (electrical, optical, chemical, mechanical, . . . ) or materials (in liquid, gas, solid, plasma form) to implanted systems and devices (ISAD). This feature can be used for powering implanted systems and devices (ISAD) with high functionality and computation power, securely communicating with implanted systems and devices (ISAD) with vital duties, and transferring materials for refilling the tanks in implanted systems and devices (ISAD) or for transferring some material from inside body to outside without requiring invasive operations.

BRIEF DESCRIPTION OF THE DRAWINGS

Embodiments of the present invention are described, by way of example only, with reference to the attached Figures, wherein.

DETAILED DESCRIPTION OF THE INVENTION

The present invention directs to a system and method for transferring signals (electrical, optical, electromagnetic, chemical, mechanical, magnetic, and similar signals used for delivering energy, data messages and to control, monitor, sense, treat, heat or cool, and for any other applications) and materials (in any shape in solid, liquid, gas, plasma forms used for delivering energy, data messages, blood and its components, medications, clinical samples and to heat or cool, drain, control, monitor, sense, treat and for any other applications) between outside and inside body through oral cavity in a human being or animal.

Figure 1:
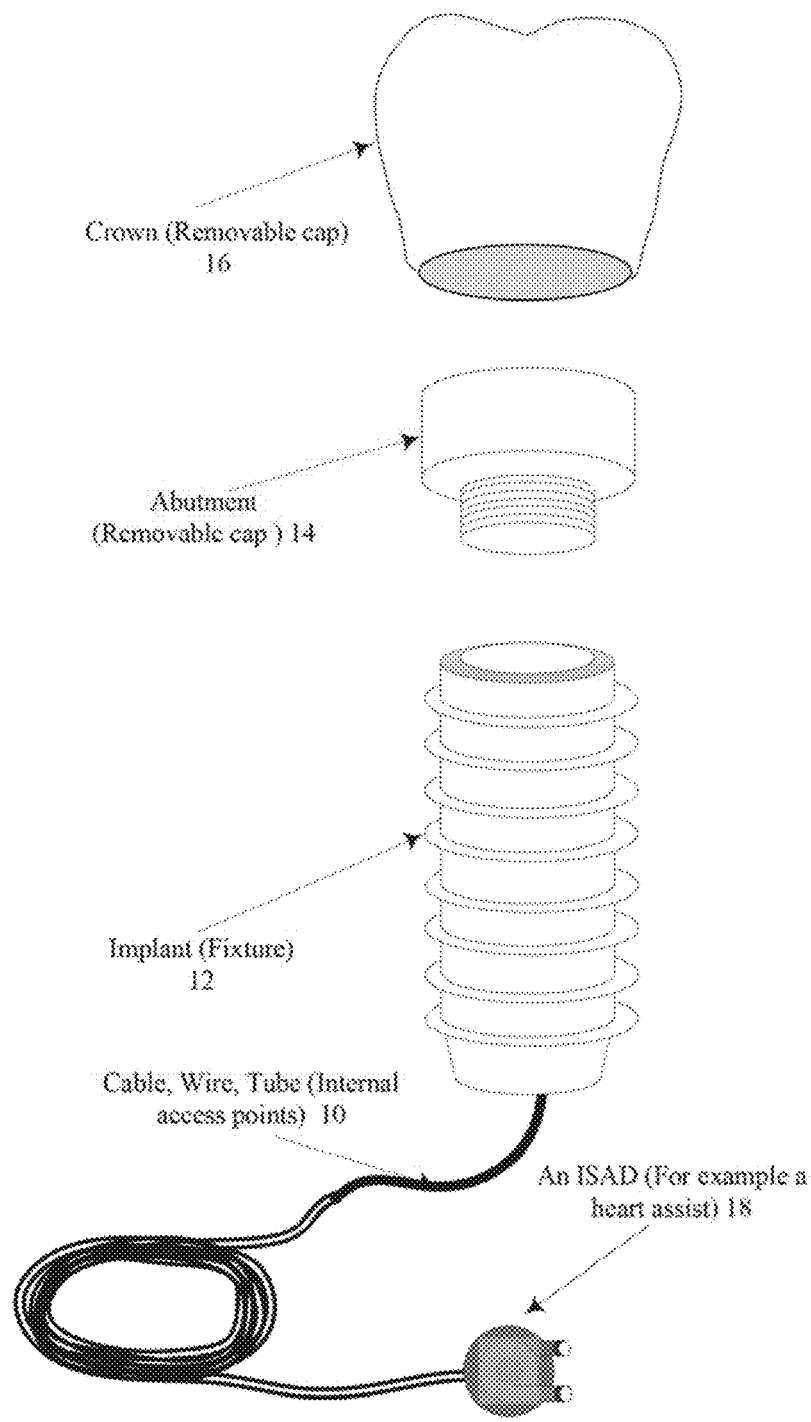
FIG. 1 is a gateway for sending and receiving signals and materials to and from inside body using a modified dental implant where wires, cable, tubes can pass through the fixture to access to an ISAD, which for example can be a heart assist.

FIG. 1 shows an embodiment of the invention as a gateway for sending and receiving signals and materials to and from inside body. The gateway resembles a modified dental implant that is placed in jawbone but it can be decided not to take any load during chewing by properly sizing the crown 16 compared with the adjacent teeth. A conduit, such as a cable, wire, tube 10 goes to the implant (fixture) 12 and from the other side said cable, wire, tube is connected to implanted devices and systems (ISAD) 18 to carry signals and materials of interest. Abutment 14 is screwed to said implant 12 and said crown 16 is attached to said abutment 14 mechanically or chemically or by other means.

Figure 2:
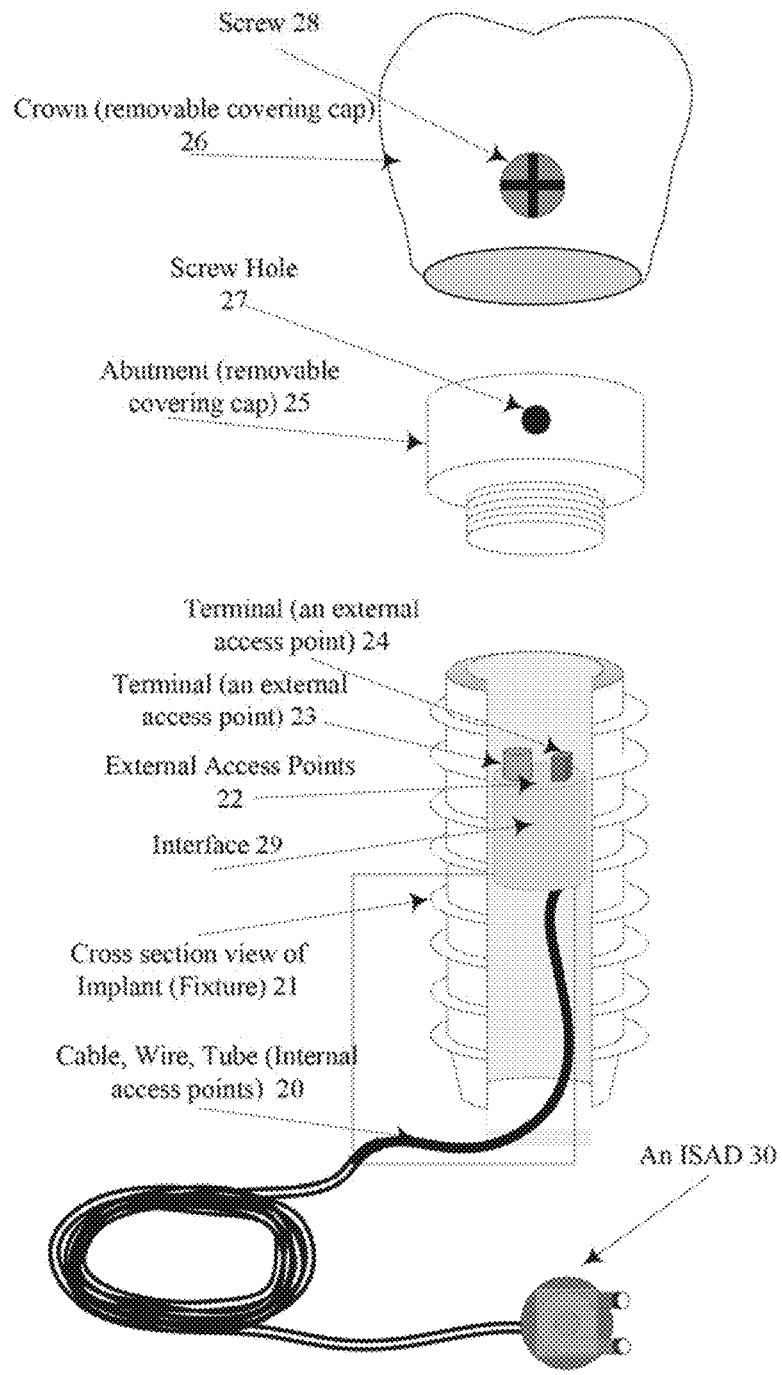
FIG. 2 depicts a cross section of an embodiment of said gateway in FIG. 1.

FIG. 2 shows an embodiment of the invention and illustrates a cross section of the gateway as a special case of the embodiment in FIG. 1. Cable, wire, tube 20 is connected to the external access point 22 via an interface 29, which is located inside the implant 21. One or a plurality of terminals 23 and 24 are located in said external access point 22 to facilitate transferring signals or materials and will be connected to an external source or sink for the signal and materials (not shown in the figure). Said terminals are of the suitable form for performing this task for the signals and materials of interest. Abutment 25 is screwed to said implant 21. The crown 26 is attached to said abutment 25 by the screw 28 that goes to the screw hole 27.

Figure 3:
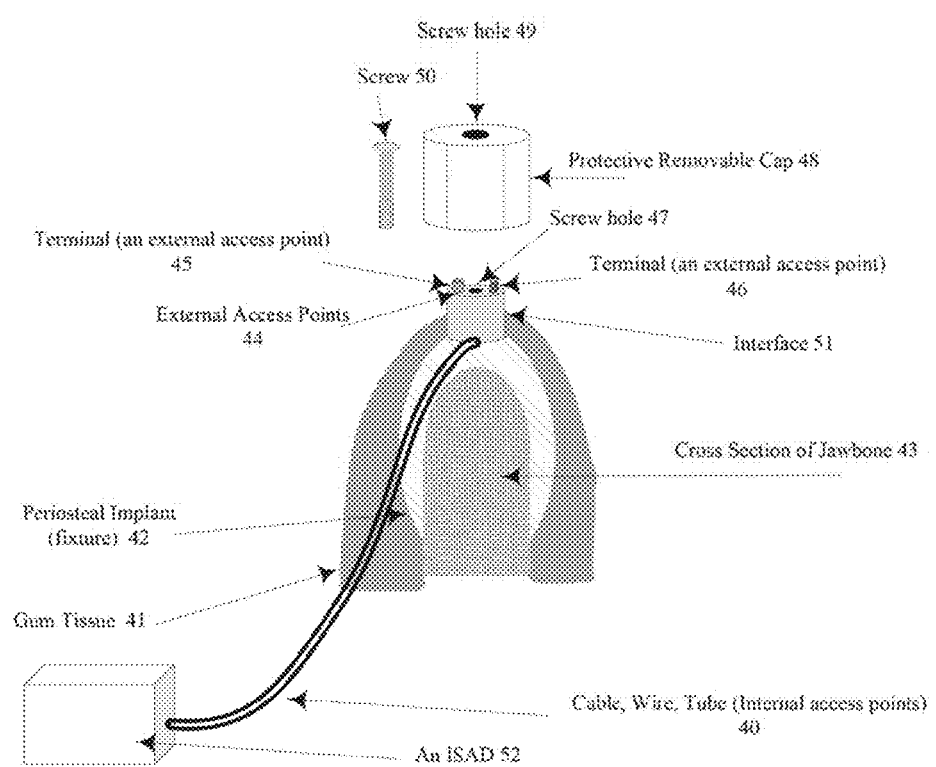
FIG. 3 shows an embodiment of the invention when the gateway is located on top of a bone.

FIG. 3 shows an embodiment of the invention resembling a gateway that is not placed inside a bone and resembles a modified periosteal implant. The altered periosteal implant 42 is placed on top of the jawbone 43 and below the gum tissues 41. The external access point 44 is placed on top of said periosteal implant 42 and is connected to implanted devices and systems (ISAD) 52 via interface 51 and the cable, wire, tube 40. The terminal 45 and 46 facilitate transferring signals and materials and will be connected to an external source or sink for the signal and materials (not shown in the figure). The protective cap 48 is attached to said external access point 44 to isolate and protect the terminals 45 and 46 and said external access points 44 in the oral cavity.

Figure 4:
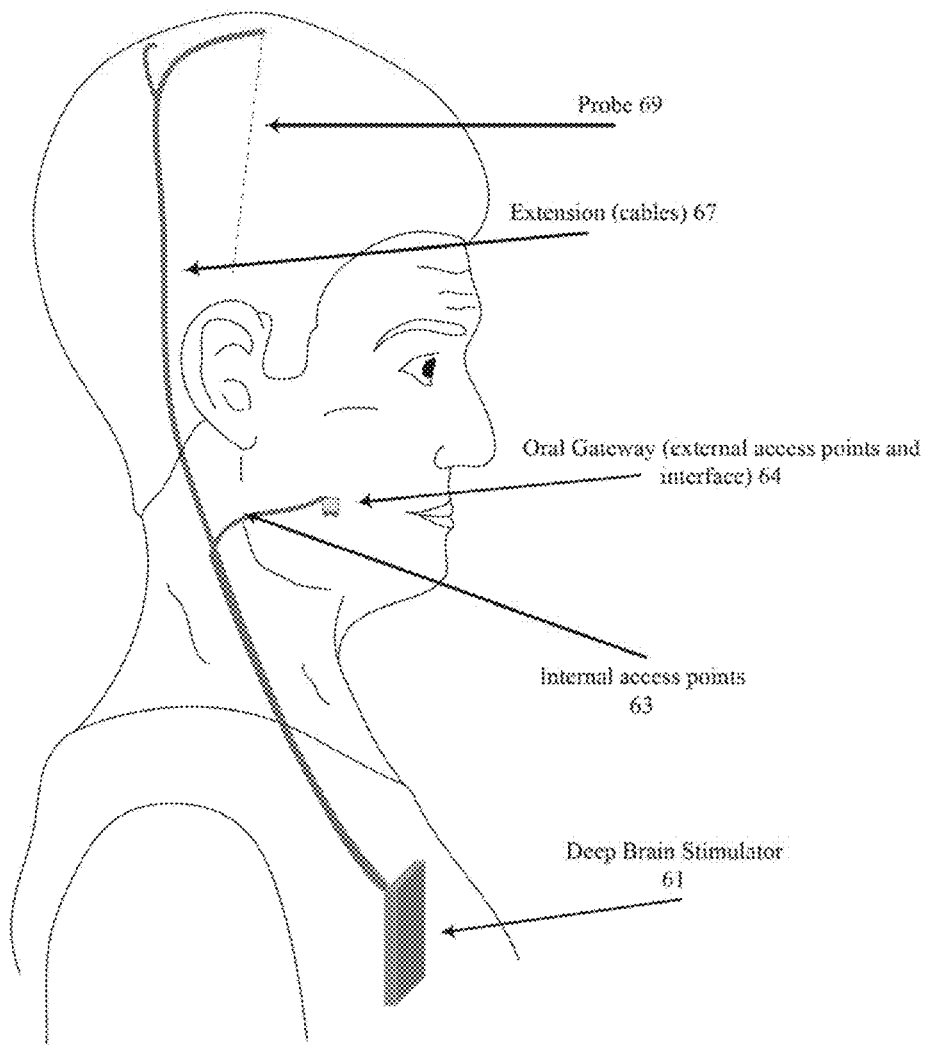
FIG. 4 shows an embodiment of the invention when the internal access points of said oral gateway in FIG. 3 are connected to a deep brain stimulator.

FIG. 4 shows an example application of the invention when the said oral gateway 44 and 51 in FIGS. 3 and 64 in FIG. 4 is used with an ISAD which is a deep brain stimulator 61. Said deep brain stimulator is connected to two probes 69 inside brain via extensions (cables) 67 that is placed inside the body and go from chest to neck and head. Said oral gateway 64 is also connected to said deep brain stimulator 61 via internal access points 63. External access points in said oral gateway 64 can be connected to a charger or deep brain stimulator control to charge batteries in said deep brain stimulator whenever it is necessary.

Figure 5:
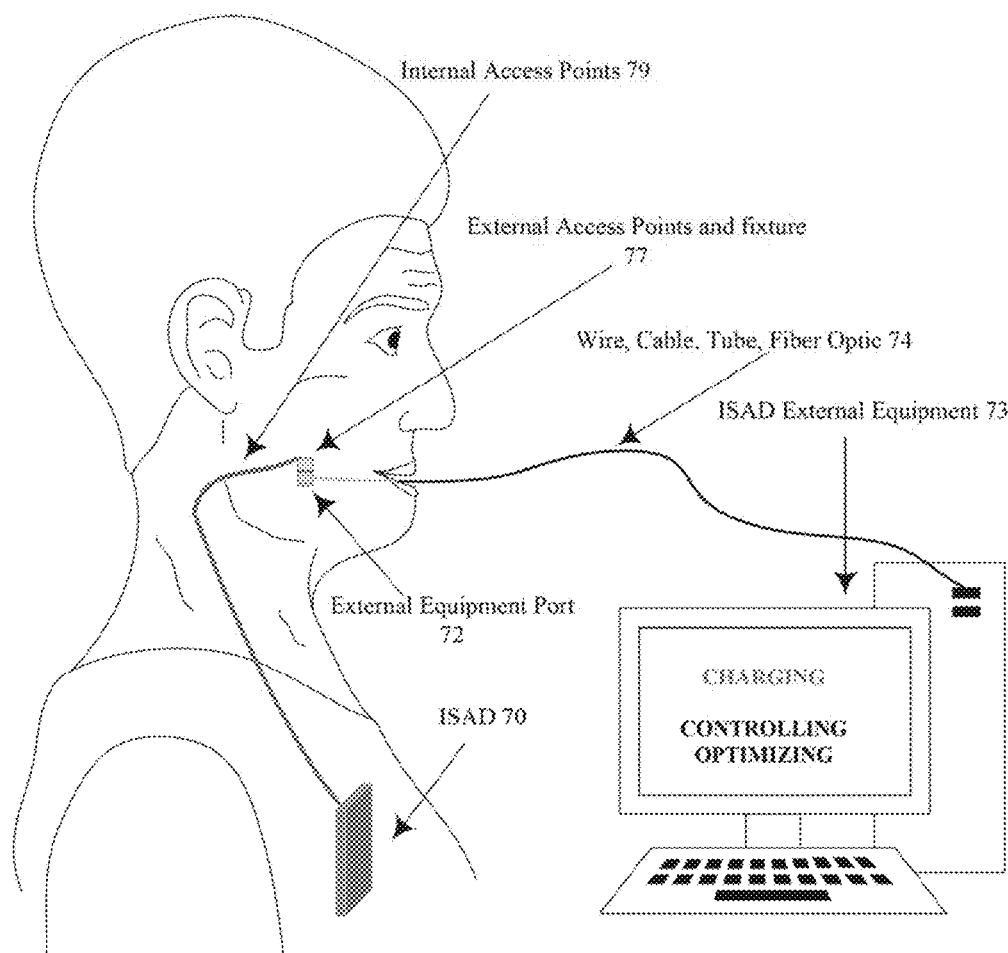
FIG. 5 shows an embodiment of the invention when the external access point of said oral gateway in FIG. 4 is connected to an ISAD external equipment.

FIG. 5 shows an example application of the invention when an ISAD 70 is connected to external access points and fixture 77 via internal access points 79. Said external access points are plugged into external equipment port 72 which is connected to an ISAD external equipment 73 via wire, cable, tube, fiber optic 74 to charge, control, and optimize the performance of said ISAD 70.

The above-described embodiments of the present invention are intended solely to be supportive illustrative examples. Any modification, variation, alteration can be effected by any skilled person in the art without departing from the scope of the present invention and accordingly the depicted embodiments shall not be utilized to limit the scope of protection provided by the claims.

CITATION LIST

1—US Patent Documents

United States Patent: US 2010/0143871 A1
J. Lee Berger
Feb. 4, 2010
Electrical Dental Screw Implant
U.S. Pat. No. 9,044,617
Aghassian
Jun. 2, 2015
External charger for a medical implantable device using field inducing coils to improve coupling
U.S. Pat. No. 8,010,205
Rahman, et al.
Aug. 30, 2011
Multiple telemetry and/or charging coil configurations for an implantable medical device system
U.S. Pat. No. 6,553,263
Meadows, et al.
Apr. 22, 2003
Implantable pulse generators using rechargeable zero-volt technology lithium-ion batteries
U.S. Pat. No. 9,039,753
Thramann
May 26, 2015
System and method to electrically charge implantable devices
U.S. Pat. No. 7,898,096
Krupenkin
Mar. 1, 2011
Method and apparatus for energy harvesting using microfluidics
U.S. Pat. No. 7,235,098
Palmaz
Jun. 26, 2007
Medical devices having MEMs functionality and methods of making same U.S. Pat. No. 9,026,212
Imran
May 5, 2015
Energy harvesting mechanism for medical devices
U.S. Pat. No. 8,311,632
Pless, et al.
Nov. 13, 2012
Devices, methods, and systems for harvesting energy in the body
U.S. Pat. No. 7,629,727
Whinnery
Dec. 8, 2009
Scalable tubular mechanical energy harvesting device
U.S. Pat. No. 7,292,888
Deno, et al.
Nov. 6, 2007
Cardiac stimulation during a refractory period
U.S. Pat. No. 6,438,408
Mulligan, et al.
Aug. 20, 2002
Implantable medical device for monitoring congestive heart failure
U.S. Pat. No. 6,317,631
Ben-Haim, et al.
Nov. 13, 2001
Controlling heart performance using a non-excitatory electric field
U.S. Pat. No. 6,024,567
Callan
Feb. 15, 2000
Dental prosthesis
U.S. Pat. No. 5,779,480
Groll, et al.
Jul. 14, 1998
Prosthetic abutment for dental implants
U.S. Pat. No. 5,674,069
Osorio
Oct. 7, 1997
Customized dental abutment
U.S. Pat. No. 8,118,596
Niznick
Feb. 21, 2012
One-piece, screw-receiving, externally-threaded endosseous dental implants and related transfer components, comfort caps and abutments
U.S. Pat. No. 7,338,286
Porter, et al.
Mar. 4, 2008
Dental implant system
U.S. Pat. No. 7,291,013
Aravena, et al.
Nov. 6, 2007
Organic shaped interface for dental implant devices
U.S. Pat. No. 6,857,874
Kim
Feb. 22, 2005
Dental implant structure
U.S. Pat. No. 6,648,643
Hollander, et al.
Nov. 18, 2003
Dental implant/abutment interface and system having prong and channel interconnections 2—Other Documents D. Halperin, et. Al, "Security and Privacy for Implantable Medical Devices," Pervasive Computing, IEEE (Volume: 7, Issue: 1), pp. 30-39, January-March 2008.

Yeun-Ho Joung, "Development of Implantable Medical Devices: From an Engineering Perspective," Int Neurourol J. 2013 September; 17(3): 98-106.

C. Andersson, "Active Implantable Medical Devices: Winning the Power Struggle," European Medical Device Technology, March/April 2012, Volume 3, No. 2

What is claimed and desired to be secured is as follows:

1. An oral cavity gateway, comprising:
a gateway comprising a fixture adapted to be secured in an oral cavity of a human body, wherein the fixture forms a path between an external area outside the body and an internal area inside the body, an interface having an external side and an internal side opposite the external side, wherein the interface is disposed within the fixture and forms a barrier between the external side proximate the oral cavity and the internal area on the internal side of the interface proximate the internal area, wherein the interface further includes an internal access point on the internal side of the barrier, an external access point on the external side of the interface, and a path between the external access point and the internal access point,
a conduit having a first end and a second end opposite the first end, wherein the conduit is connected at the first end to the internal access point of the gateway,
an implanted device located within the human body, wherein the implanted device operates independently of the gateway for at least some periods of time and the implanted device is not in direct physical contact with the gateway, and wherein the implanted device is in indirect communication with the internal access point through the conduit connected to the implanted device at the second end of the conduit, and
external equipment located in the external area and adapted to provide support to the implanted device, wherein the external equipment accesses the implanted device by connection to the external access point of the gateway.

2. The oral cavity gateway according to claim 1 wherein the fixture is secured to a bone in the oral cavity.

3. The oral cavity gateway according to claim 2 wherein the fixture is further secured in a tooth.

4. The oral cavity gateway according to claim 1 wherein the conduit comprises an electrically conductive wire.

5. The oral cavity gateway according to claim 1 wherein the conduit comprises a tube capable of transporting substances from the external equipment to the implanted device.

6. The oral cavity gateway according to claim 1 further comprising an abutment removably attached to the external side of the fixture.

7. The oral cavity gateway according to claim 6 wherein the abutment further comprises a bottom and a top, wherein the abutment is removably attached to the external side of the fixture at the bottom of the abutment, and wherein a crown is mounted to the top of the abutment.

8. A system for establishing an oral cavity gateway between an internal area inside an animal body and an external area outside of the animal body, comprising:
a gateway comprising a fixture adapted to be secured in an oral cavity of an animal, wherein the fixture forms a path between an external area outside the animal and an internal area inside the animal, an interface having an external side and an internal side opposite the external side, wherein the interface is disposed within the fixture and forms a barrier between the external side proximate the oral cavity and the internal area on the internal side of the interface proximate the internal area, wherein the interface further includes an internal access point on the internal side of the barrier, an external access point on the external side of the interface, and a path between the external access point and the internal access point, a conduit having a first end and a second end opposite the first end, wherein the conduit is connected at the first end to the internal access point of the gateway, an implanted device located within the animal, wherein the implanted device is not in direct physical contact with the gateway, and wherein the implanted device is in indirect communication with the internal access point through the conduit connected to the implanted device at the second end of the conduit, and external equipment located in the external area and adapted to provide support to the implanted device, wherein the external equipment accesses the implanted device by connection to the external access point of the gateway.

\* \* \* \* \*